United States Patent
Amari et al.

(10) Patent No.: US 11,497,290 B2
(45) Date of Patent: *Nov. 15, 2022

(54) METHOD FOR PRODUCING COATING FILM ON SKIN BY ELECTROSTATIC SPRAYING

(71) Applicant: Kao Corporation, Tokyo (JP)

(72) Inventors: Naomi Amari, Haga-gun (JP); Takehiko Tojo, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,936

(22) PCT Filed: Oct. 17, 2016

(86) PCT No.: PCT/JP2016/080674
§ 371 (c)(1),
(2) Date: Apr. 17, 2018

(87) PCT Pub. No.: WO2017/069079
PCT Pub. Date: Apr. 27, 2017

(65) Prior Publication Data
US 2019/0053602 A1  Feb. 21, 2019

(30) Foreign Application Priority Data

Oct. 19, 2015 (JP) .............................. JP2015-205932

(51) Int. Cl.
| | |
|---|---|
| A61K 8/34 | (2006.01) |
| A61Q 1/02 | (2006.01) |
| A45D 34/04 | (2006.01) |
| A61K 8/81 | (2006.01) |
| B05D 1/04 | (2006.01) |
| A61Q 1/00 | (2006.01) |
| A61L 26/00 | (2006.01) |
| A61K 8/31 | (2006.01) |
| A61Q 19/00 | (2006.01) |
| A61K 8/02 | (2006.01) |
| A61K 8/35 | (2006.01) |
| A61K 8/63 | (2006.01) |
| A61M 35/00 | (2006.01) |
| B05B 5/16 | (2006.01) |
| B05B 5/00 | (2006.01) |

(52) U.S. Cl.
CPC .............. *A45D 34/04* (2013.01); *A61K 8/02* (2013.01); *A61K 8/31* (2013.01); *A61K 8/34* (2013.01); *A61K 8/35* (2013.01); *A61K 8/63* (2013.01); *A61K 8/81* (2013.01); *A61L 26/00* (2013.01); *A61M 35/00* (2013.01); *A61Q 1/00* (2013.01); *A61Q 1/02* (2013.01); *A61Q 19/00* (2013.01); *B05B 5/00* (2013.01); *B05B 5/1691* (2013.01); *B05D 1/04* (2013.01); *A61K 2800/805* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 5,268,166 A | 12/1993 | Barnett et al. | |
| 5,494,674 A | 2/1996 | Barnett et al. | |
| 5,997,887 A * | 12/1999 | Ha ........................... | A61K 8/26 424/401 |
| 6,252,129 B1 * | 6/2001 | Coffee .............. | A61F 13/00085 239/3 |
| 6,461,626 B1 | 10/2002 | Rabe et al. | |
| 6,514,504 B1 | 2/2003 | Yen et al. | |
| 6,531,142 B1 | 3/2003 | Rabe et al. | |
| 7,078,046 B1 | 7/2006 | Rabe et al. | |
| 7,823,809 B2 * | 11/2010 | Yamaguchi ............. | B05B 5/005 128/200.14 |
| 2001/0003148 A1 | 6/2001 | Coffee | |
| 2002/0155069 A1 | 10/2002 | Pruche et al. | |

(Continued)

FOREIGN PATENT DOCUMENTS

| | | |
|---|---|---|
| JP | 5-194145 A | 8/1993 |
| JP | 2003-506470 A | 2/2003 |

(Continued)

OTHER PUBLICATIONS

International Search Report dated Dec. 20, 2016 in PCT/JP2016/080674, filed on Oct. 17, 2016.

(Continued)

*Primary Examiner* — Tigabu Kassa
(74) *Attorney, Agent, or Firm* — Oblon, McClelland, Maier & Neustadt, L.L.P.

(57) ABSTRACT

The present invention provides a coating formation method with which adhesion between skin and a coating formed by electrostatic spraying is enhanced. The coating formation method of the present invention includes a liquid agent applying step of applying a liquid agent containing one or more selected from water, polyols and oils that are in a liquid form at 20° C., and an electrostatic spraying step of electrostatically spraying a composition directly on skin to form a coating. The liquid agent applying step and the electrostatic spraying step are performed in this order or in a reversed order. The composition includes a component (a) and a component (b) below:

(a) one or more volatile substances selected from the group consisting of water, alcohols, and ketones, and
(b) a polymer having a coating formation ability.

20 Claims, 1 Drawing Sheet

(56) References Cited

U.S. PATENT DOCUMENTS

| | | |
|---|---|---|
| 2002/0192252 A1 | 12/2002 | Ying Yen et al. |
| 2003/0059599 A1 | 3/2003 | Beckley et al. |
| 2004/0076649 A1* | 4/2004 | Blin .................. A61K 8/02 |
| | | 424/401 |
| 2006/0235351 A1 | 10/2006 | Matsumura et al. |
| 2007/0060666 A1* | 3/2007 | Taniguchi ............ B65B 3/326 |
| | | 523/105 |
| 2008/0119772 A1 | 5/2008 | Coffee |
| 2009/0004252 A1* | 1/2009 | Lowndes ............. A61K 8/02 |
| | | 424/443 |
| 2010/0112019 A1* | 5/2010 | Thevenet ............ A61Q 1/02 |
| | | 424/401 |
| 2010/0022421 A1 | 9/2010 | Rabe et al. |
| 2010/0224209 A1 | 9/2010 | Rabe et al. |
| 2010/0224211 A1 | 9/2010 | Rabe et al. |
| 2010/0286591 A1 | 11/2010 | Coffee |
| 2012/0164195 A1 | 6/2012 | Zheng et al. |
| 2013/0058880 A1* | 3/2013 | Dong ................. C08K 5/5419 |
| | | 424/63 |

FOREIGN PATENT DOCUMENTS

| | | |
|---|---|---|
| JP | 2003-506474 A | 2/2003 |
| JP | 2003-507166 A | 2/2003 |
| JP | 2004-501177 A | 1/2004 |
| JP | 2006-77031 A | 3/2006 |
| JP | 2006-95332 A | 4/2006 |
| JP | 2006-104211 A | 4/2006 |
| JP | 2006-296511 A | 11/2006 |
| JP | 4077035 B2 | 4/2008 |
| JP | 4130678 B2 | 8/2008 |
| JP | 2010-270334 A | 12/2010 |
| JP | 2012-515062 A | 7/2012 |
| WO | WO 01/12139 A1 | 2/2001 |
| WO | WO 01/12335 A1 | 2/2001 |
| WO | WO 01/26610 * | 4/2001 |

OTHER PUBLICATIONS

Extended European Search Report dated Apr. 18, 2019 in Patent Application No. 16857394.7, 8 pages.

Database GNPD, Mintel; "Treatment Clear Base", Retrieved from www.gnpd.com, XP55578649, Database accession No. 2045608, Apr. 16, 2013, 5 pages.

Database GNPD, Mintel; "Makeup Setting Spray", Retrieved from www.gnpd.com, XP55578800, Database accession No. 3377203, Aug. 18, 2015, 3 pages.

U.S. Appl. No. 15/768,998, filed Apr. 17, 2018, Naomi Amari, et al.

* cited by examiner

METHOD FOR PRODUCING COATING FILM ON SKIN BY ELECTROSTATIC SPRAYING

TECHNICAL FIELD

The present invention relates to a coating formation method.

BACKGROUND ART

Various methods for forming a coating by electrostatic spraying are known. For example, Patent Literature 1 describes a method for treating skin, the method including electrostatically spraying a composition on the skin. The composition used in this method includes an electrically insulating liquid material, a conductive substance, a particulate powder material, and a thickener. Cosmetics that contain a pigment, and compositions for skin care are typically used as this composition. Specifically, cosmetic foundation is used as this composition. That is, the invention described in Patent Literature 1 is intended to be mainly used to electrostatically spray the cosmetic foundation and apply the cosmetic foundation on the skin for the purpose of beauty treatment.

Patent Literature 2 describes a disposable cartridge to be used in an electrostatic spraying apparatus for cosmetics. This electrostatic spraying apparatus is a hand-held and self-contained type. This electrostatic spraying apparatus is used to spray cosmetic foundation as in Patent Literature 1 above.

CITATION LIST

Patent Literature

Patent Literature 1: U.S. Pat. No. 6,531,142B1
Patent Literature 2: WO01/12335A1

SUMMARY OF INVENTION

When a coating is formed on skin by performing electrostatic spraying according to the methods described in Patent Literatures 1 and 2, the adhesion between the skin and the coating formed by electrostatic spraying is insufficient, and thus the coating may be damaged or come off due to an external force such as friction.

The present invention relates to a coating formation method for forming a coating on a surface of skin.

The coating formation method of the present invention includes
a liquid agent applying step of applying, on skin, a liquid agent containing at least one member selected from water, polyols and oils that are in a liquid form at 20° C.; and
an electrostatic spraying step of electrostatically spraying a composition directly on the skin to form a coating,
wherein the liquid agent applying step and the electrostatic spraying step are performed in this order or in a reversed order, and
the composition includes component (a) and component (b) below:
(a) one or more volatile substances selected from the group consisting of water, alcohols, and ketones, and
(b) a polymer having a coating formation ability.

DESCRIPTION OF EMBODIMENTS

Figure 1:
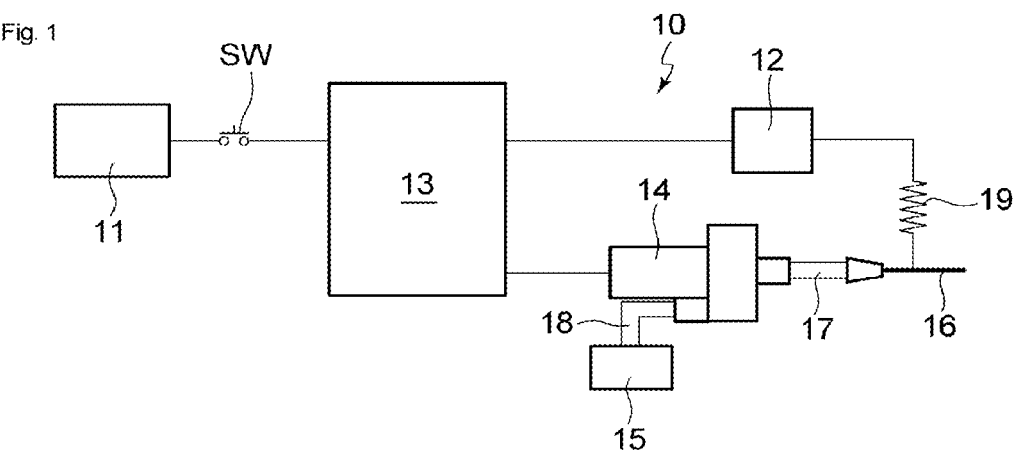
FIG. 1 is a schematic diagram illustrating a configuration of an electrostatic spraying apparatus to be preferably used in the present invention.

The present invention relates to improvement of a technology of the method for electrostatic splaying on skin. The present invention further relates to improvement of the adhesion of the coating formed on the skin by electrostatic spraying.

Hereinafter, the present invention will be described based on a preferred embodiment thereof with reference to the drawings. In the present invention, a coating is formed by applying a composition including predetermined components directly on skin. In the present invention, an electrostatic spraying method is used as a coating formation method. The electrostatic spraying method is a method in which a positive or negative high voltage is applied to a composition to electrify the composition, and then the electrified composition is sprayed toward a spray object. The sprayed composition spreads in a space while being repeatedly micronized due to Coulomb repulsion, and during this process or after the composition attaches to the spray object, a solvent, which is a volatile substance, dries to form a coating on the surface of the spray object.

The above-mentioned composition (this composition is also referred to as "spray composition" hereinafter) used in the present invention is in a liquid form in the environment where the electrostatic spraying method is performed. This composition includes component (a) and component (b) below:
(a) one or more volatile substances selected from water, alcohols, and ketones, and
(b) a polymer having a coating formation ability.

Hereinafter, each composition will be described.

A volatile substance to be used as the component (a) is a substance having volatility in a liquid form. The component (a) is blended into the spray composition for the purpose of forming a dry coating in the following manner: when the spray composition, which has been placed in an electric field and sufficiently electrified, is discharged toward skin from the tip of a nozzle, the charge density of the spray composition becomes excessive as the component (a) evaporates, and then the component (a) further evaporates while the spray composition is further micronized due to Coulomb repulsion. For this purpose, the vapor pressure of the volatile substance at 20° C. is preferably 0.01 kPa or more and 106.66 kPa or less, more preferably 0.13 kPa or more and 66.66 kPa or less, even more preferably 0.67 kPa or more and 40.00 kPa or less, and even more preferably 1.33 kPa or more and 40.00 kPa or less.

Preferable examples of alcohols serving as the volatile substance to be used as the component (a) include chain aliphatic monohydric alcohols, cyclic aliphatic monohydric alcohols, and aromatic monohydric alcohols. Specific examples thereof include ethanol, isopropyl alcohol, butyl alcohol, phenylethyl alcohol, propanol, and pentanol. One or more alcohols selected from these alcohols can be used.

Examples of ketones serving as the volatile substance to be used as the component (a) include acetone, methyl ethyl ketone, and methyl isobutyl ketone. These ketones can be used alone or in combination of two or more.

The volatile substance to be used as the component (a) is more preferably at least one member selected from ethanol, isopropyl alcohol, butyl alcohol and water, even more preferably at least one member selected from ethanol and butyl alcohol, and even more preferably ethanol.

The spray composition contains, along with the component (a), a polymer having a coating formation ability to be used as the component (b). The polymer having a coating formation ability to be used as the component (b) is commonly a substance that can be dissolved in the volatile substance to be used as the component (a). The term "dissolve" as used herein refers to a state in which a substance is in a dispersed state at 20° C. and the dispersion is uniform when visually observed, and preferably transparent or translucent when visually observed.

As the polymer having a coating formation ability, a polymer is used that is appropriate according to the properties of the volatile substance to be used as the component (a). Specifically, polymers having a coating formation ability are roughly classified into water-soluble polymers and water-insoluble polymers. The term "water-soluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, 0.5 g or more of the immersed polymer dissolves in the water. On the other hand, the term "water-insoluble polymer" as used herein refers to a polymer having a property such that when 1 g of the polymer is weighed out and immersed in 10 g of ion-exchanged water in an environment at a pressure of 1 atmosphere and a temperature of 23° C. for 24 hours, more than 0.5 g of the immersed polymer does not dissolve in the water.

Examples of the water-soluble polymers having a coating formation ability include naturally-occurring macromolecules such as pullulan, hyaluronic acid, chondroitin sulfate, poly-γ-glutamic acid, modified corn starch, β-glucan, glucooligosaccharide, mucopolysaccharide such as heparin and keratosulfate, cellulose, pectin, xylan, lignin, glucomannan, galacturonic acid, *psyllium* seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose, hydroxypropyl methyl cellulose; and synthetic macromolecules such as partially saponified polyvinyl alcohol (when not used in combination with a cross-linking agent), low saponified polyvinyl alcohol, polyvinyl pyrrolidone (PVP), polyethylene oxide, and sodium polyacrylate. These water-soluble polymers can be used alone or in combination of two or more. It is preferable to use pullulan and the synthetic macromolecules such as partially saponified polyvinyl alcohol, low saponified polyvinyl alcohol, polyvinyl pyrrolidone, and polyethylene oxide, of these water-soluble polymers, from the viewpoint of easily manufacturing the coating. When polyethylene oxide is used as the water-soluble polymer, its number average molecular weight is preferably 50,000 or more and 3,000,000 or less, and more preferably 100,000 or more and 2,500,000 or less.

On the other hand, examples of the water-insoluble polymers having a coating formation ability include completely saponified polyvinyl alcohol, which can be insolubilized after the formation of a coating; partially saponified polyvinyl alcohol, which can be cross-linked after the formation of a coating when used in combination with a cross-linking agent; oxazoline modified silicone such as a poly(N-propanoylethyleneimine)-grafted dimethyl siloxane/γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; and a polyamideimide resin. These water-insoluble polymers can be used alone or in combination of two or more. It is preferable to use completely saponified polyvinyl alcohol, which can be insolubilized after the formation of a coating, partially saponified polyvinyl alcohol, which can be cross-linked after the formation of the coating when used in combination with a cross-linking agent, a polyvinyl butyral resin, oxazoline modified silicone such as a poly(N-propanoylethyleneimine)-grafted dimethyl siloxane/γ-aminopropylmethylsiloxane copolymer, water-soluble polyester, zein, and the like, of these water-insoluble polymers.

The content of the component (a) in the spray composition is preferably 50 mass % or more, more preferably 55 mass % or more, and even more preferably 60 mass % or more. In addition, the content of the component (a) in the spray composition is preferably 98 mass % or less, more preferably 96 mass % or less, and even more preferably 94 mass % or less. The content of the component (a) in the spray composition is preferably 50 mass % or more and 98 mass % or less, more preferably 55 mass % or more and 96 mass % or less, and even more preferably 60 mass % or more and 94 mass % or less. When the component (a) is blended into the spray composition in this proportion, the spray composition can sufficiently volatilize when the electrostatic spraying method is performed.

On the other hand, the content of the component (b) in the spray composition is preferably 2 mass % or more, more preferably 4 mass % or more, and even more preferably 6 mass % or more. In addition, the content of the component (b) in the spray composition is preferably 50 mass % or less, more preferably 45 mass % or less, and even more preferably 40 mass % or less. The content of the component (b) in the spray composition is preferably 2 mass % or more and 50 mass % or less, more preferably 4 mass % or more and 45 mass % or less, and even more preferably 6 mass % or more and 40 mass % or less. When the component (b) is blended into the spray composition in this proportion, a desired coating can be successfully formed.

The spray composition may include only the above-described component (a) and component (b) or may include other components in addition to the component (a) and the component (b). Examples of the other components include a plasticizer for the polymer having a coating formation ability to be used as the component (b), a coloring pigment, an extender pigment, a dye, a surfactant, a UV protection agent, a flavoring agent, a repellent, an antioxidant, a stabilizer, an antiseptic, and various vitamins. When the spray composition includes the other components, the blend proportion of the other components is preferably 0.1 mass % or more and 30 mass % or less, and more preferably 0.5 mass % or more and 20 mass % or less.

When the electrostatic spraying method is performed, the viscosity of the spray composition used in this method is preferably 1 mPa·s or more, more preferably 10 mPa·s or more, and even more preferably 50 mPa·s or more, at 25° C. In addition, the viscosity of the spray composition is preferably 5,000 mPa·s or less, more preferably 2,000 mPa·s or less, and even more preferably 1,500 mPa·s or less, at 25° C. The viscosity of the spray composition is preferably 1 mPa·s or more and 5,000 mPa·s or less, more preferably 10 mPa·s or more and 2,000 mPa·s or less, and even more preferably 50 mPa·s or more and 1,500 mPa·s or less, at 25° C. When the spray composition having a viscosity in this range is used, a porous coating, particularly a porous coating including a deposit of fibers, can be successfully formed with the electrostatic spraying method. The formation of the porous coating is advantageous from the viewpoint of preventing skin from getting sweaty. The viscosity of the spray composition is measured at 25° C. with an E-type viscometer. An E-type viscometer manufactured by Tokyo Keiki Inc. can be used as the E-type viscometer, for example. In this case, a rotor No. 43 can be used as a rotor.

The spray composition is sprayed directly on human skin, which is a spray object, in the electrostatic spraying method. The electrostatic spraying method includes a step of electrostatically spraying the spray composition on the skin using an electrostatic spraying apparatus. FIG. 1 is a schematic diagram illustrating a configuration of an electrostatic spraying apparatus to be preferably used in the present invention. An electrostatic spraying apparatus 10 shown in this diagram includes a low-voltage power source 11. The low-voltage power source 11 can generate a voltage of several volts to a dozen or so volts. It is preferable that the low-voltage power source 11 is constituted by one or more batteries for the purpose of enhancing the portability of the electrostatic spraying apparatus 10. Also, when a battery is used as the low-voltage power source 11, there is an advantage in that the battery can be easily replaced as necessary. An AC adapter or the like can be used as the low-voltage power source 11 instead of the battery.

The electrostatic spraying apparatus 10 also includes a high-voltage power source 12. The high-voltage power source 12 is connected to the low-voltage power source 11 and includes an electric circuit (not shown) that boosts a voltage generated by the low-voltage power source 11 to a high voltage. A voltage boosting electric circuit usually includes a transformer, a capacitor, a semiconductor element, and the like.

The electrostatic spraying apparatus 10 further includes an auxiliary electric circuit 13. The auxiliary electric circuit 13 intervenes between the above-described low-voltage power source 11 and high-voltage power source 12 and has a function of adjusting the voltage of the low-voltage power source 11 to allow the high-voltage power source 12 to stably operate. Furthermore, the auxiliary electric circuit 13 has a function of controlling the rotation rate of a motor provided in a micro gear pump 14, which will be described later. The amount of the spray composition supplied from a container 15 for the spray composition, which will be described later, to the micro gear pump 14 is controlled by controlling the rotation rate of the motor. A switch SW is installed between the auxiliary electric circuit 13 and the low-voltage power source 11, and the operation of the electrostatic spraying apparatus 10 can be started/stopped by turning on/off the switch SW.

The electrostatic spraying apparatus 10 further includes a nozzle 16. The nozzle 16 is made of a conductor including various conductors typified by metal or a non-conductor such as plastic, rubber, or ceramic and has a shape allowing the spray composition to be discharged from the tip of the nozzle. A minute space through which the spray composition flows and that extends in the longitudinal direction of the nozzle 16 is formed inside the nozzle 16. With regard to the size of the cross section of this minute space, the diameter thereof is preferably 100 μm or more and 1,000 μm or less. The nozzle 16 is in communication with the micro gear pump 14 via a duct 17. The duct 17 may be made of a conductor or a non-conductor. The nozzle 16 is electrically connected to the high-voltage power source 12. This makes it possible to apply a high voltage to the nozzle 16. In this case, in order to prevent a case where excessive current flows when a human body is in direct contact with the nozzle 16, the nozzle 16 is electrically connected to the high-voltage power source 12 via a current limiting resistor 19.

The micro gear pump 14, which is in communication with the nozzle 16 via the duct 17, functions as a supply device for supplying the spray composition accommodated in the container 15 to the nozzle 16. The low-voltage power source 11 supplies power to the micro gear pump 14, so that the micro gear pump 14 operates. The micro gear pump 14 is configured to supply a predetermined amount of the spray composition to the nozzle 16 under the control of the auxiliary electric circuit 13.

The container 15 is connected to the micro gear pump 14 via a flexible duct 18. The spray composition is accommodated in the container 15. It is preferable that the container 15 is an exchangeable cartridge-type.

Figure 2:
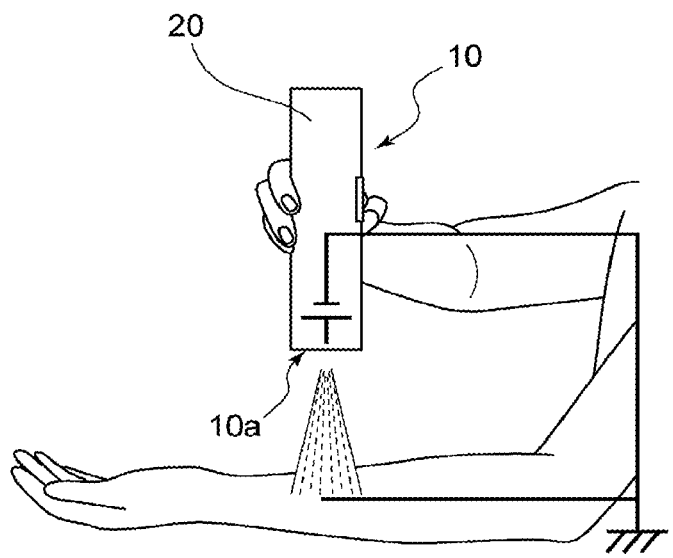
FIG. 2 is a schematic diagram illustrating a state in which an electrostatic spraying apparatus is used to perform an electrostatic spraying method.

The electrostatic spraying apparatus 10 configured as described above can be used as shown in FIG. 2, for example. FIG. 2 shows the hand-held electrostatic spraying apparatus 10 having dimensions allowing the apparatus to be held by one hand. In the electrostatic spraying apparatus 10 shown in this diagram, all of the members shown in the configuration diagram in FIG. 1 are accommodated in a cylindrical housing 20. The nozzle (not shown) is arranged at one end 10a in the longitudinal direction of the housing 20. The nozzle is arranged in the housing 20 in such a manner that the direction in which the composition is discharged matches the longitudinal direction of the housing 20 and the nozzle projects toward the skin. Since the tip of the nozzle is arranged so as to project toward the skin in the longitudinal direction of the housing 20, the spray composition is less likely to adhere to the housing, and the coating can be stably formed.

When the electrostatic spraying apparatus 10 is operated, a user, that is, a person who forms a coating on his/her skin by electrostatic spraying, holds the apparatus 10 by the hand and directs the one end 10a of the apparatus 10 at which the nozzle (not shown) is arranged toward a portion to be subjected to electrostatic spraying. FIG. 2 shows a state in which the one end 10a of the electrostatic spraying apparatus 10 is directed to the inner side of the forearm of the user. Under these conditions, the apparatus 10 is switched on to perform the electrostatic spraying method. When the apparatus 10 is turned on, an electric field is generated between the nozzle and the skin. In the embodiment shown in FIG. 2, a high positive voltage is applied to the nozzle, and the skin serves as a negative electrode. When the electric field is generated between the nozzle and the skin, the spray composition at the tip of the nozzle is polarized by electrostatic induction, thus shaping the tip of the spray composition into a cone shape. Then, electrified droplets of the spray composition at the tip of the nozzle are discharged to the air from the tip of the cone toward the skin along the electric field. When the component (a) used as a solvent evaporates from the electrified spray composition, which has been discharged to the air, the charge density of the surface of the spray composition becomes excessive, and the spray composition spreads in the space while being repeatedly micronized due to Coulomb repulsion and then reaches the skin. In this case, by appropriately adjusting the viscosity of the spray composition, it is possible to cause the sprayed composition to reach the skin in the state in which the composition is in a droplet form. Alternatively, while the composition is being discharged to the space, it is also possible to evaporate the volatile substance used as a solvent from the composition, solidify the polymer having a coating formation ability used as a solute to form fibers while the fibers are stretched and deformed due to an electric potential difference, and deposit the fibers on the surface of the skin. When the viscosity of the spray composition is increased, for example, it is easy to deposit the composition in a fibrous form on the surface of the skin. Accordingly, a porous coating including the deposit of fibers is formed on the surface of the skin. The porous coating including the deposit of fibers can also be formed by adjusting the distance between the nozzle and the skin, and the voltage applied to the nozzle.

A high electric potential difference is generated between the nozzle and the skin while the electrostatic spraying method is being performed. However, an impedance is very large, and therefore, a current flowing in a human body is extremely small. The inventors of the present invention confirmed that a current flowing in a human body while the electrostatic spraying method is being performed is smaller by several digits than a current flowing in a human body due to static electricity generated in normal life, for example.

When the deposit of fibers is formed with the electrostatic spraying method, the thickness of the fibers expressed as a diameter of a corresponding circle is preferably 10 nm or more, and more preferably 50 nm or more. In addition, the thickness is preferably 3,000 nm or less, and more preferably 1,000 nm or less. The thickness of the fibers can be measured by observing the fibers magnified 10,000 times using a scanning electron microscopy (SEM), for example, removing defects (mass of fibers, intersection of fibers, and droplets) from the two-dimensional images of the fibers, selecting any ten fibers, drawing a line orthogonal to the longitudinal direction of each of the fibers, and reading the diameter of the fiber directly.

Although the above-mentioned fiber is a continuous fiber having an infinite length in the formation principle, it is preferable that the fiber has a length at least 100 times longer than its thickness. In this specification, a fiber having a length over 100 times than its thickness is defined as a "continuous fiber". It is preferable that a coating formed with the electrostatic spraying method is a porous discontinuous coating including the deposit of continuous fibers. The coating in such a form can be treated as one sheet including an aggregate and is characterized by being very soft, and therefore, there is an advantage in that the coating is unlikely to fall apart even when a shearing force is applied to the coating, and the coating has a good property of following to body movement. Also, there is an advantage in that the coating has a good property of diffusing sweat from the skin. Furthermore, there is an advantage in that the coating is easy to take off. In contrast, a continuous coating having no pores is not easy to take off and has a very low property of diffusing sweat. Therefore, the skin is likely to get sweaty.

The fibrous spray composition reaches the skin in a state in which the composition is electrified. Since the skin is also electrified as described above, the fibers come into intimate contact with the skin due to an electrostatic force. Since there is minute unevenness such as a skin texture on the surface of the skin, an anchor effect is obtained due to the unevenness, and the fibers thus come into further intimate contact with the surface of the skin. After the electrostatic spraying is finished in this manner, the electrostatic spraying apparatus 10 is turned off. Accordingly, the electric field between the nozzle and the skin vanishes, and the electric charge on the surface of the skin is fixed. As a result, the coating exhibits a better adhesion.

Although, as the coating, the porous coating including the deposit of fibers has been described above, the form of the coating is not limited thereto. A continuous coating having no pores may be formed, and a porous coating in a form other than the deposit of fibers, for example, a porous coating obtained by forming a plurality of through pores irregularly or regularly in a continuous coating, that is, a discontinuous coating, may be formed. As described above, a coating having a desired shape can be formed by adjusting the viscosity of the spray composition, the distance between the nozzle and the skin, the voltage applied to the nozzle, and the like.

Although the distance between the nozzle and the skin depends on the voltage applied to the nozzle, the distance of 50 mm or more and 150 mm or less is preferable in order to successfully form the coating. The distance between the nozzle and the skin can be measured using a commonly used non-contact sensor or the like.

Whether or not the coating formed with the electrostatic spraying method is a porous coating, the basis weight of the coating is preferably 0.1 $g/m^2$ or more, and more preferably 1 $g/m^2$ or more. In addition, the basis weight of the coating is preferably 30 $g/m^2$ or less, and more preferably 20 $g/m^2$ or less. For example, the basis weight of the coating is preferably 0.1 $g/m^2$ or more and 30 $g/m^2$ or less, and more preferably 1 $g/m^2$ or more and 20 $g/m^2$ or less. Setting the basis weight of the coating in this manner makes it possible to improve the adhesion of the coating. The electrostatic spraying step of electrostatically spraying a composition directly on skin to form a coating refers to a step of electrostatically spraying on the skin or on the skin on which the above-described liquid have been applied (may simply be referred to as skin), thereby forming a coating. A step of electrostatically spraying a composition on a region other than the skin, thereby forming a sheet composed of fibers, and then applying the sheet to the skin is different from the above-described electrostatic spraying step.

The present invention includes a liquid agent applying step of applying, on skin, a liquid agent containing at least one member selected from water, polyols and oils that are in a liquid form at 20° C. prior to or subsequent to or both prior to and subsequent to an electrostatic spraying step of forming the coating with the above-described electrostatic spraying. When the liquid agent is applied prior to the electrostatic spraying step, the surface of the skin is more easily polarized by electrostatic induction. Therefore, the sprayed spray composition is likely to more firmly adhere thereto due to an electrostatic force, and the transparency of the external appearance of the sprayed spray composition can be improved. When the liquid agent applying step is performed subsequent to the electrostatic spraying step, particularly immediately subsequent to the electrostatic spraying step, the coating formed in the electrostatic spraying step easily bonds with the skin due to the liquid agent. Therefore, the coating comes into highly intimate contact with the skin, and the transparency is further improved. A level difference is unlikely to be generated between the end portion of the coating and the skin, and thus the adhesion between the coating and the skin is improved. As a result, even when the coating is formed on a portion such as a joint in which the degree of expansion and contraction of skin is large and a portion such as a shoulder whose curvature is large, the coating is unlikely to come off or break. When the coating is transparent, colored and transparent, or translucent, the skin serving as a foundation is hardly concealed. Preferably, when the coating is a porous coating including the deposit of fibers, the adhesion to the skin is high despite being of a high porosity, and a large capillary force is likely to be generated. Furthermore, use of fine fibers makes it easy to increase the specific surface area of the porous coating.

By performing the liquid agent applying step prior to and/or subsequent to the step of forming a porous coating including the deposit of fibers in the electrostatic spraying step, a moisturizing liquid agent holding coating in which a moisturizing liquid agent is present between the fibers included in the porous coating and/or on the surfaces of the fibers is formed. Accordingly, the adhesion of the coating is improved, and the transparency of the coating is maintained or improved. In particular, when the coating is colorless and transparent or translucent, the coating is difficult to visually confirm, and thus can be made to look like a natural skin. When the coating is colored and opaque, the coating has a feeling of transparency and thus can be made to look like part of the skin. It should be noted that "colored" mentioned above includes a white color.

When the liquid agent to be used in the liquid agent applying step includes water, examples of the liquid agent include water-based liquids such as water, an aqueous solution, and an aqueous dispersion. Also, examples thereof include a lotion, a milky lotion including an emulsion such as an O/W emulsion and a W/O emulsion, a cosmetic cream, and an aqueous liquid thickened using a thickener.

When the liquid agent to be used in the liquid agent applying step includes a polyol. The polyol includes alkylene glycols such as ethylene glycol, propylene glycol, 1,3-propanediol, and 1,3-butandiol; polyalkylene glycols such as diethylene glycol, dipropylene glycol, polyethylene glycol and polypropylene glycol; glycerins such as glycerin, diglycerin and triglycerin. From the viewpoint of usability such as smooth application, the polyol preferably includes ethylene glycol, polyethylene glycol, 1,3-butandiol, dipropylene glycol, polyethylene glycol, glycerin and diglycerin. The polyol more preferably includes propylene glycol and 1,3-butandiol.

On the other hand, when the liquid agent to be used in the liquid agent applying step includes an oil that is in a liquid form at 20° C. (this oil is also referred to as "liquid oil" hereinafter), examples of the oil, which is in a liquid form at 20° C., include linear or branched hydrocarbon oils such as liquid paraffin, light isoparaffin, liquid isoparaffin, squalane, and squalene; ester oils such as a plant oil including jojoba oil and olive oil, an animal oil including liquid lanolin, monoalcohol fatty acid ester, and polyhydric alcohol fatty acid ester; and silicone oils such as dimethylpolysiloxane, dimethylcyclopolysiloxane, methylphenylpolysiloxane, methylhydrogenpolysiloxane, and higher alcohol modified organopolysiloxane. Of these, from the viewpoint of usability such as smooth application, the hydrocarbon oils and polar oils such as the ester oils, the plant oils containing a triglyceride etc., and the silicone oils are preferable, and the hydrocarbon oils, the ester oils, and the triglyceride are more preferable. The liquid oils selected from these oils can be used alone or in combination of two or more.

Examples of the above-mentioned hydrocarbon oils include liquid paraffin, squalane, squalene, n-octane, n-heptane, cyclohexane, light isoparaffin, and liquid isoparaffin, and liquid paraffin and squalane are preferable from the viewpoint of usability. The viscosities of the hydrocarbon oils at 30° C. are preferably 10 mPa·s or more, and more preferably 30 mPa·s or more, from the viewpoint of bringing the electrostatically sprayed coating into intimate contact with the skin. From these viewpoints, the total content of isododecane, isohexadecane, and hydrogenated polyisobutene, which have a viscosity of less than 10 mPa·s at 30° C., in the liquid agent is preferably 10 mass % or less, more preferably 5 mass % or less, even more preferably 1 mass % or less, and even more preferably 0.5 mass % or less, or alternatively, none of these oils need to be contained in the liquid agent.

Similarly, from the viewpoint of making the coating by the electrostatic spraying come into highly intimate contact with the skin, viscosity of the ester oil and the silicon oil is preferably 10 mPa·s or more, and more preferably 30 mPa·s or more at 30° C.

Here, the viscosity is measured using a BM type viscometer (manufactured by Tokimec Inc.; measurement condition: rotor No. 1, 60 rpm, 1 minute) at 30° C. It should be noted that from the same viewpoint, the total content of ether oils such as cetyl-1,3-dimethyl butyl ether, dicapryl ether, dilauryl ether, diisostearyl ether in the liquid agent is preferably 10 mass % or less, more preferably 5 mass % or less, and even more preferably 1 mass % or less.

Polar oils that are in a liquid form at 20° C. can be preferably used as the above-mentioned liquid oil, and examples thereof include ester oils, plant oils (triglycerides), higher alcohols of branched fatty acids or unsaturated fatty acids, antiseptics, and silicone oils. These liquid oils can be used alone or in combination of two or more.

Examples of the above-mentioned ester oils include esters between a linear or branched fatty acid and a linear or branched alcohol or a polyhydric alcohol. Specific examples thereof include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythrite tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalene dicarboxylic acid, (12- to 15-carbon) alkyl benzoate, cetearylisononanoate, glycerin tri(caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, glyceryl tri-palmoil fatty acid, castor oil fatty acid methyl ester, oleyl oleate, 2-heptylundecyl palmitate, diisobutyl adipate, N-lauroyl-L-glutamate-2-octyldodecyl ester, di-2-heptylundecyl adipate, ethyllaurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, 2-ethylhexyl p-methoxycinnamate, and tripropylene glycol dipivalate. From the viewpoint of making the coating by the electrostatic spraying come into highly intimate contact with the skin, and from the viewpoint of great feeling when applied on the skin, the ester oil preferably includes at least one ester oil selected from octyldodecyl myristate, myristyl myristate, isocetyl stearate, isocetyl isostearate, cetearylisononanoate, diisobutyl adipate, di-2-ethylhexyl sebacate, isopropyl myristate, isopropyl palmitate, diisostearyl malate, neopentyl glycol dicaprate, (12- to 15-carbon) alkyl benzoate, and glycerin tri(caprylate/caprate). The ester oil more preferably includes at least one ester oil selected from isopropyl myristate, isopropyl palmitate, diisostearyl malate, neopentyl glycol dicaprate, (12- to 15-carbon) alkyl benzoate, and glycerin tri(caprylate/caprate). The ester oil even more preferably includes at least one ester oil selected from neopentyl glycol dicaprate, (12- to 15-carbon) alkyl benzoate, and glycerin tri(caprylate/caprate).

Fatty acid triglycerides are preferable as the triglyceride, and are contained in olive oil, jojoba oil, macadamia nut oil, meadowfoam oil, castor oil, safflower oil, sunflower oil, avocado oil, canola oil, apricot kernel oil, rice germ oil, and rice oil, for example.

Examples of the higher alcohols include liquid higher alcohols having 12 to 20 carbon atoms, and specific examples thereof include isostearyl alcohol and oleyl alcohol.

Examples of the antiseptics include phenoxyethanol, methyl p-hydroxybenzoate, ethyl p-aminobenzoate, isobutyl p-hydroxybenzoate, isopropyl p-hydroxybenzoate, ethyl p-hydroxybenzoate, butyl p-hydroxybenzoate, propyl p-hydroxybenzoate, benzyl p-hydroxybenzoate, and ethyl hexanediol.

Examples of the silicone oils include dimethylpolysiloxane, dimethylcyclopolysiloxane, methylphenylpolysiloxane, methylhydrogenpolysiloxane, and higher alcohol modified organopolysiloxane. From the viewpoint of the adhesion of the liquid agent of the present invention to the skin, the content of the silicone oil in the liquid agent is preferably 10 mass % or less, more preferably 5 mass % or less, even more preferably 1 mass % or less, and even more preferably 0.1 mass % or less.

The kinetic viscosities of the silicone oils at 25° C. are preferably 3 mm$^2$/s or more, more preferably 4 mm$^2$/s or more, and even more preferably 5 mm$^2$/s or more, and are preferably 30 mm$^2$/s or less, more preferably 20 mm$^2$/s or less, and even more preferably 10 mm$^2$/s or less, from the viewpoint of bringing the electrostatically sprayed coating into intimate contact with the skin.

From the viewpoint of bringing the electrostatically sprayed coating into intimate contact with the skin, the silicon oil preferably includes dimethylpolysiloxane.

It is preferable that the liquid agent contains the liquid oil, and the content of the liquid oil in the liquid agent is preferably 0.1 mass % or more, more preferably 0.5 mass % or more, and even more preferably 5 mass % or more. In addition, the content of the liquid oil in the liquid agent is preferably 100 mass % or less. The content of the liquid oil in the liquid agent is preferably 0.1 mass % or more and 100 mass % or less, more preferably 0.5 mass % or more and 100 mass % or less, and even more preferably 5 mass % or more and 100 mass % or less.

Furthermore, it is preferable that the liquid agent contains the liquid oil or polyol, and the content of the liquid oil or polyol in the liquid agent is preferably 0.1 mass % or more, more preferably 0.5 mass % or more, and even more preferably 5 mass % or more. In addition, the content of the liquid oil or the polyol in the liquid agent is preferably 100 mass % or less. The content of the liquid oil in the liquid agent is preferably 0.1 mass % or more and 100 mass % or less, more preferably 0.5 mass % or more and 100 mass % or less, and even more preferably 5 mass % or more and 100 mass % or less.

When the liquid agent contains the polar oil, it is preferable that the liquid agent contains water and the polar oil from the viewpoint of enhancing the adhesion of the coating to the skin, and the total content of water and the polar oil in the liquid agent is preferably 40 mass % or more and 100 mass % or less. Also, from the viewpoint of stability, the liquid agent may contain a surfactant, a polymer, and a thickener, and from the viewpoint of improving the adhesion to the skin and the moisturizing performance with respect to the coating, the liquid agent may contain an oil agent that is in a solid form at 30° C., such as vaseline, cetanol, stearyl alcohol, and ceramide.

Similarly, when the liquid agent contains the polyol, it is preferable that the liquid agent contains water and the polyol from the viewpoint of enhancing the adhesion of the coating to the skin, and the total content of water and the polyol in the liquid agent is preferably 40 mass % or more and 100 mass % or less. Also, from the viewpoint of stability, the liquid agent may contain a surfactant, a polymer, and a thickener, and from the viewpoint of improving the adhesion to the skin and the moisturizing performance with respect to the coating, the liquid agent may contain an oil agent that is in a solid form at 30° C., such as vaseline, cetanol, stearyl alcohol, and ceramide.

Even when one of water, polyol and the liquid oil is used in the liquid agent, it is preferable that the liquid agent has a viscosity of about 5,000 mPa·s or less at 25° C. from the viewpoint of improving the adhesion of the coating formed with the electrostatic spraying method to the skin. The viscosity of the liquid is measured with the method as described above.

Furthermore, from the viewpoint of improving the adhesion of the coating formed with the electrostatic spraying method to the skin, the content of the coloring pigments in the liquid is preferably 0.1 mass % or less, more preferably 0.05 mass % or less, and even more preferably 0.001 mass % or less. In the present invention, the coloring pigment includes no transparent pigment, and includes white pigment.

The liquid agent including water or the liquid oil can be applied on the skin with various methods. For example, a thin layer of the liquid agent can be formed by applying the liquid agent on the skin with a dripping method, a sprinkling method, or the like, and performing a step of spreading the liquid agent to cause the liquid agent to bond with the skin or the coating. In the step of spreading the liquid agent, a method such as smearing using the user's own finger, a tool such as an applicator, or the like can be applied, for example. Although it is sufficient if the liquid agent is merely dripped or sprinkled, performing the spreading step makes it possible to cause the liquid agent to bond with the skin or the coating, thus making it possible to sufficiently improve the adhesion of the coating. As another method, a thin layer of the liquid agent can be formed by spraying the liquid agent on the skin. In this case, it is not particularly necessary to separately spread the liquid agent, but a spreading operation may be performed after spraying. It should be noted that when the liquid agent is applied after the coating is formed, a sufficient amount of the liquid agent is applied on the skin, and excessive liquid agent can be removed by performing a step of bringing a sheet material into contact with an area on which the liquid agent has been applied.

It is sufficient if the amount of the liquid agent applied on the skin or the coating is set to be a necessary and sufficient amount with which the adhesion between the skin and the coating is improved. When the liquid agent contains the liquid oil, from the viewpoint of obtaining reliable adhesion between the skin and the coating, the amount of the liquid agent applied on the skin is set such that the basis weight of the liquid oil is preferably 0.1 g/m$^2$ or more, and more preferably 0.2 g/m$^2$ or more, and in addition, the basis weight of the liquid oil is preferably 40 g/m$^2$ or less, and more preferably 35 g/m$^2$ or less. The amount of the liquid agent applied on the skin is set such that the basis weight of the liquid oil is preferably 0.1 g/m² or more and 40 g/m² or less, and more preferably 0.2 g/m² or more and 35 g/m² or less.

From the viewpoint of improving the adhesion between the skin and the coating and improving the transparency, the amount of the liquid agent applied on the skin or the coating is preferably 5 g/m² or more, more preferably 10 g/m² or more, and even more preferably 15 g/m² or more, and in addition, the amount is preferably 50 g/m² or less, and more preferably 45 g/m² or less.

Furthermore, the cosmetics other than the liquid agent may be applied on the skin before or after the liquid agent is applied on the skin.

The coating formation method as described above is useful as various beauty treatment methods that are not intended to be used as a method of operation, treatment, or diagnosis of a human body. For the purpose of beauty treatment, the coating formation method according to the present invention can be applied to whitening of skin, concealment of specks on skin, concealment of dullness/dark areas of skin, concealment of wrinkles of skin, shading of skin, protection of skin from ultraviolet rays, and moisturization of skin, for example. Alternatively, the coating formation method according to the present invention can also be applied to various actions for protecting skin that are domestically and individually performed, such as protection of various wounds including an abrasion, a cut wound, a laceration wound, a puncture wound, and the like, and prevention of a bedsore.

Although the present invention has been described based on the preferred embodiment above, the present invention is not limited to the above-mentioned embodiment. In the above-mentioned embodiment, a person who wants to form a coating on his/her skin holds the electrostatic spraying apparatus 10 and generates an electric field between the nozzle of the apparatus 10 and his/her skin, for example. However, a person who wants to form a coating on his/her skin need not hold the electrostatic spraying apparatus 10 as long as an electric field is generated between the nozzle and the skin.

With respect to the above-described embodiment, the present invention further discloses the following aspects of the coating formation method.

<1>

A coating formation method for forming a coating on a surface of skin, comprising:
a liquid agent applying step of coating, on skin, a liquid agent containing at least one member selected from water, polyols and oils that are in a liquid form at 20° C.; and an electrostatic spraying step of electrostatically spraying a composition directly on the skin to form a coating,
wherein the liquid agent applying step and the electrostatic spraying step are performed in this order or in a reversed order, and
the composition includes component (a) and component (b) below:
(a) one or more volatile substances selected from the group consisting of water, alcohols, and ketones, and
(b) a polymer having a coating formation ability.

<2>

The coating formation method as set forth in clause <1>, wherein in the electrostatic spraying step, the composition is electrostatically sprayed on the skin to form a porous coating.

<3>

The coating formation method as set forth in clause <1> or <2>,
wherein in the electrostatic spraying step, a porous coating including a deposit of fibers is formed, and then
in the liquid agent applying step, the liquid agent is coated on the porous coating to form a liquid agent holding coating in which the liquid agent is present between the fibers included in the porous coating and/or on the surfaces of the fibers.

<4>

The coating formation method as set forth in any one of clauses <1> to <3>,
wherein in the liquid agent applying step, the liquid agent is coated on the coating to maintain transparency of the coating.

<5>

The coating formation method as set forth in any one of clauses <1> to <4>,
wherein in the electrostatic spraying step, an electrostatic spraying apparatus is used to electrostatically spray the composition on the skin to form a porous coating including a deposit of fibers, and
the electrostatic spraying apparatus comprises:
a container in which the composition is accommodated;
a nozzle from which the composition is discharged;
a supply device that supplies the composition accommodated in the container to the nozzle; and
a power source that applies a voltage to the nozzle.

<6>

The coating formation method as set forth in any one of clauses <1> to <5>, wherein the vapor pressure of the volatile substance of (a) at 20° C. is preferably 0.01 kPa or more and 106.66 kPa or less, more preferably 0.13 kPa or more and 66.66 kPa or less, even more preferably 0.67 kPa or more and 40.00 kPa or less, and even more preferably 1.33 kPa or more and 40.00 kPa or less.

<7>

The coating formation method as set forth in any one of clauses <1> to <6>, wherein the volatile substance of (a) is alcohol,
chain aliphatic monohydric alcohols, cyclic aliphatic monohydric alcohols, and aromatic monohydric alcohols are preferably used as the alcohol, these alcohols can be used alone or in combination of two or more, and
ethanol, isopropyl alcohol, butyl alcohol, phenylethyl alcohol, propanol, and pentanol are particularly preferably used as the alcohol.

<8>

The coating formation method as set forth in any one of clauses <1> to <7>, wherein the volatile substance of (a) is at least one member selected from ethanol, isopropyl alcohol, butyl alcohol, and water, preferably at least one member selected from ethanol and butyl alcohol, and more preferably ethanol.

<9>

The coating formation method as set forth in any one of clauses <1> to <8>, wherein the polymer of (b) having a coating formation ability is a substance that can be dissolved in the volatile substance of (a) and includes water-soluble polymers and water-insoluble polymers, and here, the term "dissolve" refers to a state in which a substance is in a dispersed state at 20° C. and the dispersion is uniform when visually observed, and preferably transparent or translucent when visually observed.

<10>

The coating formation method as set forth in any one of clauses <1> to <9>, wherein the water-soluble polymers having a coating formation ability are one or more water-soluble macromolecules selected from naturally-occurring polymers such as pullulan, hyaluronic acid, chondroitin sulfate, poly-γ-glutamic acid, modified corn starch, β-glucan, glucooligosaccharide, mucopolysaccharide such as heparin and keratosulfate, cellulose, pectin, xylan, lignin, glucomannan, galacturonic acid, *psyllium* seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose, hydroxypropyl methyl cellulose; partially saponified polyvinyl alcohol (when not used in combination with a cross-linking agent); low saponified polyvinyl alcohol; polyvinyl pyrrolidone (PVP); polyethylene oxide; and sodium polyacrylate, and preferably one or more water-soluble macromolecules selected from pullulan, partially saponified polyvinyl alcohol, low saponified polyvinyl alcohol, polyvinyl pyrrolidone, and polyethylene oxide.

<11>

The coating formation method as set forth in any one of clauses <1> to <9>, wherein the water-insoluble polymers having a coating formation ability are one or more water-insoluble polymers selected from completely saponified polyvinyl alcohol, which can be insolubilized after the formation of a coating; partially saponified polyvinyl alcohol, which can be cross-linked after the formation of a coating when used in combination with a cross-linking agent; oxazoline modified silicone such as a poly(N-propanoylethyleneimine)-grafted dimethyl siloxane/γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; and a polyamideimide resin, and preferably one or more water-insoluble polymers selected from completely saponified polyvinyl alcohol, which can be insolubilized after the formation of a coating, partially saponified polyvinyl alcohol, which can be cross-linked after the formation of the coating when used in combination with a cross-linking agent, a polyvinyl butyral resin, oxazoline modified silicone such as a poly(N-propanoylethyleneimine)-grafted dimethylsiloxane/γ-aminopropylmethylsiloxane copolymer, water-soluble polyester, and zein.

<12>

The coating formation method as set forth in any one of clauses <1> to <11>, wherein the content of the component (a) in the composition is preferably 50 mass % or more, more preferably 55 mass % or more, and even more preferably 60 mass % or more, the content of the component (a) in the composition is preferably 98 mass % or less, 96 mass % or less, and 94 mass % or less, and the content of the component (a) in the composition is preferably 50 mass % or more and 98 mass % or less, more preferably 55 mass % or more and 96 mass % or less, and even more preferably 60 mass % or more and 94 mass % or less.

<13>

The coating formation method as set forth in any one of clauses <1> to <12>, wherein the content of the component (b) in the composition is preferably 2 mass % or more, more preferably 4 mass % or more, and even more preferably 6 mass % or more, the content of the component (b) in the composition is preferably 50 mass % or less, more preferably 45 mass % or less, and even more preferably 40 mass % or less, and the content of the component (b) in the composition is preferably 2 mass % or more and 50 mass % or less, more preferably 4 mass % or more and 45 mass % or less, and even more preferably 6 mass % or more and 40 mass % or less.

<14>

The coating formation method as set forth in any one of clauses <1> to <13>, wherein the composition includes only the component (a) and component (b) or includes other components in addition to the component (a) and the component (b), and the other components include a plasticizer for the polymer of (b) having a coating formation ability, a coloring pigment, an extender pigment, a dye, a surfactant, a UV protection agent, a flavoring agent, a repellent, an antioxidant, a stabilizer, an antiseptic, and various vitamins.

<15>

The coating formation method as set forth in clause <14>, wherein when the composition includes the other components, the blend proportion of the other components is preferably 0.1 mass % or more and 30 mass % or less, and more preferably 0.5 mass % or more and 20 mass % or less.

<16>

The coating formation method as set forth in any one of clauses <1> to <15>, wherein the viscosity of the composition is preferably 1 mPa·s or more, more preferably 10 mPa·s or more, and even more preferably 50 mPa·s or more, at 25° C., the viscosity of the composition is preferably 5,000 mPa·s or less, more preferably 2,000 mPa·s or less, and even more preferably 1,500 mPa·s or less, at 25° C., and the viscosity of the composition is preferably 1 mPa·s or more and 5,000 mPa·s or less, more preferably 10 mPa·s or more and 2,000 mPa·s or less, and even more preferably 50 mPa·s or more and 1,500 mPa·s or less, at 25° C.

<17>

The coating formation method as set forth in any one of clauses <1> to <16>, wherein an electrostatic spraying method is performed using an electrostatic spraying apparatus, the electrostatic spraying apparatus includes the nozzle, and the nozzle is made of a conductor including various conductors typified by metal or a non-conductor such as plastic, rubber, or ceramic and has a shape allowing the composition to be discharged from the tip of the nozzle.

<18>

The coating formation method as set forth in any one of clauses <1> to <17>, wherein the electrostatic spraying method is performed using an electrostatic spraying apparatus, the electrostatic spraying apparatus includes the nozzle and a housing, the nozzle is arranged at one end, in a longitudinal direction, of the housing, and the nozzle is arranged in the housing in such a manner that the direction in which the composition is discharged matches the longitudinal direction of the housing and the nozzle projects toward the skin.

<19>

The coating formation method as set forth in any one of clauses <1> to <18>, wherein in the sprayed composition, the volatile substance used as a solvent is evaporated from droplets, and the polymer having a coating formation ability used as a solute is solidified to form fibers while the fibers are stretched and deformed due to an electric potential difference.

<20>
The coating formation method as set forth in any one of clauses <1> to <19>, wherein the electrostatic spraying method is performed using an electrostatic spraying apparatus, the electrostatic spraying apparatus includes the nozzle, and the distance between the nozzle and the skin is set to be 50 mm or more and 150 mm or less.

<21>
The coating formation method as set forth in any one of clauses <1> to <20>, wherein the basis weight of the coating formed with the electrostatic spraying method is preferably 0.1 g/m$^2$ or more, and more preferably 1 g/m$^2$ or more, the basis weight of the coating is preferably 30 g/m$^2$ or less, and more preferably 20 g/m$^2$ or less, and the basis weight of the coating is preferably 0.1 g/m$^2$ or more and 30 g/m$^2$ or less, and more preferably 1 g/m$^2$ or more and 20 g/m$^2$ or less.

<22>
The coating formation method as set forth in any one of clauses <1> to <21>, wherein when the liquid agent to be used in the liquid agent applying step includes water, examples of the liquid agent include water-based liquids such as water, an aqueous solution, and an aqueous dispersion, and examples of the liquid agent also include a lotion, a milky lotion including an emulsion such as an O/W emulsion and a W/O emulsion, a cosmetic cream, and an aqueous liquid thickened using a thickener.

<23>
The coating formation method as set forth in any one of clauses <1> to <22>, wherein when the liquid agent to be used in the liquid agent applying step includes an oil that is in a liquid form at 20° C., examples of the oil include linear or branched hydrocarbon oils such as liquid paraffin, light isoparaffin, liquid isoparaffin, squalane, and squalene; ester oils such as a plant oil including jojoba oil and olive oil, an animal oil including liquid lanolin, monoalcohol fatty acid ester, and polyhydric alcohol fatty acid ester; and silicone oils such as dimethylpolysiloxane, dimethylcyclopolysiloxane, methylphenylpolysiloxane, methylhydrogenpolysiloxane, and higher alcohol modified organopolysiloxane, and the oil is one or more selected preferably from the hydrocarbon oils and polar oils such as the ester oils, the plant oils containing a triglyceride etc., and the silicone oils, and more preferably from the hydrocarbon oils, the ester oils, and the triglyceride.

<24>
The coating formation method as set forth in any one of clauses <1> to <23>, wherein it is preferable that the liquid agent contains the liquid oil, the content of the liquid oil in the liquid agent is preferably 0.1 mass % or more, more preferably 0.5 mass % or more, and even more preferably 5 mass % or more, the content of the liquid oil in the liquid agent is preferably 100 mass % or less, and the content of the liquid oil in the liquid agent is preferably 0.1 mass % or more and 100 mass % or less, more preferably 0.5 mass % or more and 100 mass % or less, and even more preferably 5 mass % or more and 100 mass % or less.

<25>
The coating formation method as set forth in any one of clauses <1> to <24>, wherein when the liquid agent contains the polar oil, it is preferable that the liquid agent contains water and the polar oil, and that the total content of water and the polar oil is preferably 40 mass % or more and 100 mass % or less.

<26>
The coating formation method as set forth in any one of clauses <1> to <25>, wherein it is preferable that the liquid agent contains a surfactant, a polymer, and a thickener, and that the liquid agent contains an oil agent that is in a solid form at 30° C., such as vaseline, cetanol, stearyl alcohol, and ceramide.

<27>
The coating formation method as set forth in any one of clauses <1> to <26>, wherein when the liquid agent contains the liquid oil, the amount of the liquid agent applied on the skin is set such that the basis weight of the liquid oil is preferably 0.1 g/m$^2$ or more, and more preferably 0.2 g/m$^2$ or more, the basis weight is preferably 40 g/m$^2$ or less, and more preferably 35 g/m$^2$ or less, and the basis weight is preferably 0.1 g/m$^2$ or more and 40 g/m$^2$ or less, and more preferably 0.2 g/m$^2$ or more and 35 g/m$^2$ or less, and the amount of the liquid agent applied on the skin or the coating is preferably 5 g/m$^2$ or more, more preferably 10 g/m$^2$ or more, and even more preferably 15 g/m$^2$ or more, and the amount is preferably 50 g/m$^2$ or less, and more preferably 45 g/m$^2$ or less.

EXAMPLES

Hereinafter, the present invention will be described more specifically by way of examples. However, the scope of the present invention is not limited to these examples. Unless otherwise stated, "%" means "mass %".

Test 1

Example 1

(1) Preparation of Spray Composition 99.5% ethanol and 1-butanol were used as the component (a) of the spray composition. Polyacrylic acid was used as the component (b). The blend proportions of ethanol and 1-butanol used as the component (a) were 52% and 26%, respectively, and the blend proportion of the component (b) was 22%.

(2) Preparation of Liquid Agent to be Used in Liquid Agent Applying Step 55 mg of a lotion A was used as the liquid agent. Table 1 below shows the composition of the lotion A.

(3) Liquid Agent Applying Step

The above-mentioned lotion A was dripped on the inner side of a forearm of a human, spread so as to have an area having a diameter of 4 cm or more and less than 6 cm using a finger, and allowed to bond therewith, and a thin layer was thus formed. The amount of the dripped lotion A was 55 mg, and that amount was such that the presence of the lotion A could be confirmed by visual observation or by touch due to the region in which the lotion A was spread being wet or moist, or having a different texture, or the like. As a result, the amount of the lotion A applied on the skin was set such that the basis weight of the lotion A was 28.0 g/m$^2$ and the total basis weight of the liquid oil was 0.25 g/m$^2$.

(4) Electrostatic Spraying Step

The electrostatic spraying method was performed for 20 seconds toward the thin layer formed in the liquid agent applying step of (3) using the electrostatic spraying apparatus 10 having the configuration shown in FIG. 1 and the external appearance shown in FIG. 2. The electrostatic spraying method was performed under the conditions described below.

Applied voltage: 10 kV

Distance between nozzle and skin: 100 mm

Discharge amount of spray composition: 5 ml/h
Environment: 25° C., 30% RH

A porous coating including the deposit of fibers was formed on the surface of the skin with this electrostatic spraying. The coating had a circular shape having a diameter of about 4 cm, and had a mass of about 5.5 mg. The thickness of the fibers measured with the above-described method was 506 nm.

Examples 2 and 3

In Example 2, 80 mg of a cosmetic milky lotion A was used as the liquid agent to be used in a liquid agent application forming step. Table 2 below shows the composition of the cosmetic milky lotion A. In Example 3, 30 mg of a squalane oil was used as an oil A. Other than this, a porous coating including the deposit of fibers was obtained by performing the liquid agent applying step and the electrostatic spraying step in this order, in the same manner as in Example 1. The amount of the cosmetic milky lotion A applied on the skin was such that the basis weight of the cosmetic milky lotion A was 40.8 g/m$^2$ and the total basis weight of the liquid oil was 4.1 g/m$^2$, and the amount of the squalane oil applied on the skin was such that the basis weight of the oil was 15.3 g/m$^2$.

Examples 4 to 9 and Examples 19 to 21

A porous coating including the deposit of fibers was obtained by performing the liquid agent applying step and the electrostatic spraying step in this order in the same manner as in Example 1, except that the conditions shown in Table 3 and Table 4 below were used.

Examples 10 to 18 and Examples 22 to 24

In Examples 10 to 18 and Examples 22 to 24, the order of the liquid agent applying step and the electrostatic spraying step in Examples 1 to 9 and Examples 19 to 21 was reversed. Other than this, a porous coating including the deposit of fibers was obtained in the same manner as in Example 1.

Example 25

In Example 25, 100% ethanol and water was used instead of using 99.5% ethanol solution in Example 13. Other than this, a porous coating including the deposit of fibers was obtained in the same manner as in Example 1.

Comparative Examples 1 to 3

These Comparative Examples are examples in which the liquid agent applying step in Examples 1, 4 and 7 was not performed. Other than this, a porous coating including the deposit of fibers was obtained in the same manner as in Example 1.

Comparative Example 4

(1) Preparation of Spray Composition
99.5% ethanol was used as the component (a) of the spray composition.
Polyvinyl butyral was used as the component (b). Di(phytosteryl/octyl dodecyl)lauroyl glutamate was used as the other component. The blend proportion of ethanol as the component (a) was 80%, that of polyvinyl butyral as the component (b) was 14%, and that of di(phytosteryl/octyl dodecyl)lauroyl glutamate as the other component was 6%.

(2) Formation of Sheet in the Electrostatic Spraying Step
The electrostatic spraying method was performed for 20 seconds onto a stainless steel plate, using the electrostatic spraying apparatus 10 having the configuration shown in FIG. 1 and the external appearance shown in FIG. 2. The electrostatic spraying method was performed under the conditions described below.
Applied voltage: 10 kV
Distance between nozzle and skin: 100 mm
Discharge amount of spray composition: 5 ml/h
Environment: 25° C., 30% RH A porous coating composed of a deposit of fibers was formed on the surface of the stainless steel plate with this electrostatic spraying. The coating had a circular shape with a diameter of about 4 cm, and had a mass of about 5.5 mg. The thickness of the fibers measured using the above-described method was 506 nm.

(3) Liquid Agent Applying Step
The above-mentioned lotion A was dripped on the inner side of a forearm of a human, spread so as to have an area having a diameter of 4 cm or more and less than 6 cm using a finger, and allowed to bond therewith, and a thin layer was thus formed. The amount of the dripped lotion A was 55 mg, and that amount was such that the presence of the lotion A could be confirmed by visual observation or by touch due to the region in which the lotion A was spread being wet or moist, or having a different texture, or the like. As a result, the amount of the lotion A applied on the skin was set such that the basis weight of the lotion A was 28.0 g/m$^2$ and the total basis weight of the liquid oil was 0.25 g/m$^2$.

(4) Sheet Applying Step
The sheet obtained in the electrostatic spraying step (2) was detached from the stainless steel plate, softly placed on the skin onto which the foundation has been applied in the step (4), and gently pressed.

Comparative Examples 5 and 6

A porous coating including the deposit of fibers was obtained by performing the liquid agent applying step and the sheet applying step in this order, in the same manner as in Comparative Example 4, other than 80 mg of the cosmetic milky lotion A was used in Comparative Example 5 and 30 mg of squalane oil was used in Comparative Example 6 as the liquid agent to be used in a liquid agent application forming step.

Comparative Examples 7 to 9

In Comparative Examples 7 to 9, the order of the liquid agent applying step and the sheet applying step in Comparative Examples 4 to 6 was reversed. Other than this, a porous coating including of the deposit of fibers was obtained in the same manner as in Comparative Example 4.

Evaluation
With regard to the coatings formed in the examples and comparative examples, the adhesion to the skin was evaluated. The evaluation was performed by visually observing the state of the coating after a microvibration load was applied by touching the coating with a finger in a direction orthogonal to the skin and a shearing force was applied to the coating by moving a finger back and forth in a direction parallel to the skin. Table 3 and Table 4 shows the results. The following are the evaluation criteria.

1 When a microvibration load is applied by a finger in the orthogonal direction, almost all the coating comes off.

2 When a microvibration load is applied by a finger in the orthogonal direction, a portion of the fibers included in the coating come off.

3 No coming off occurs in the orthogonal direction, but when a shearing force is applied in the parallel direction, almost all the coating comes off.

4 No coming off occurs in the orthogonal direction, but when a shearing force is applied by a finger in the parallel direction, a portion of the fibers or coating comes off.

5 No coming off occurs in the orthogonal direction, and even when shearing force is applied in the parallel direction, the coating or the fibers do not come off.

TABLE 1

| Lotion A | |
|---|---|
| Component | (%) |
| Purified water | 74.308 |
| Glycerin | 10 |
| Dipropylene glycol | 4 |
| 1,3-Propanediol | 4 |
| Polyethylene glycol | 4 |
| Polyoxyethylene glucoside | 1 |
| L-Arginine | 0.001 |
| 2-(2-hydroxyethoxy)ethylguanidine succinate | 0.5 |
| pH adjusting agent | 0.15 |
| Sodium hyaluronate (aqueous solution of ethanol) | 0.1 |
| Highly polymerized polyethylene glycol | 0.001 |
| Hydroxypropyl guar gum | 0.025 |
| Xanthan gum | 0.03 |
| Polyoxyethylene octyl dodecyl ether | 0.2 |
| Silicone oil | 0.05 |
| Glyceryl monostearate monomyristate | 0.1 |
| Neopentyl glycol dicaprate | 0.1 |
| Squalane | 0.03 |
| Phenoxyethanol | 0.4 |
| Plant extract | 1 |
| Flavoring agent | 0.005 |
| Total | 100 |

TABLE 2

| Cosmetic milky lotion A | |
|---|---|
| Component | (%) |
| Purified water | 74 |
| Methylpolysiloxane | 5 |
| Ethyl p-hydroxybenzoate | 0.1 |
| Methyl p-hydroxybenzoate | 0.4 |
| 1,3-butylene glycol | 0.5 |
| Glycerin | 10 |
| Vaseline | 0.5 |
| Carboxyvinyl polymer | 0.2 |
| Neopentyl glycol dicaprate | 3.5 |
| Stearyl alcohol | 0.4 |
| Cetanol | 0.6 |
| Sodium N-stearoyl-N-methyltaurine | 0.5 |
| Sodium polyoxyethylenelauryletherphosphate | 0.3 |
| Sorbitan monostearate | 0.2 |
| Polyoxyethylenesorbitan monostearate | 0.2 |
| Ceramide | 1 |
| Plant extract | 1.5 |
| pH adjusting agent | 0.1 |
| Flavoring agent | 1 |
| Total | 100 |

TABLE 3

| | | Composition | | Portion subjected to electrostatic spraying | Liquid agent | | Adhesion evaluation |
|---|---|---|---|---|---|---|---|
| | | Component (a) (%) | Component (b) (%) | Other component | | Type | Application time | |
| Ex. | 1 | Ethanol (52) 1-Butanol (26) | Polyacrylic acid (22) | | Skin | Lotion A | Before electrostatic spraying | 4 |
| | 2 | Ethanol (52) 1-Butanol (26) | Polyacrylic acid (22) | | Skin | Cosmetic milky lotion A | Before electrostatic spraying | 4 |
| | 3 | Ethanol (52) 1-Butanol (26) | Polyacrylic acid (22) | | Skin | Oil A | Before electrostatic spraying | 4 |
| | 4 | Ethanol (80) | Polyvinyl butyral (14) | Di(phytosteryl/octyl dodecyl)lauroyl glutamate (6) | Skin | Lotion A | Before electrostatic spraying | 5 |
| | 5 | Ethanol (80) | Polyvinyl butyral (14) | Di(phytosteryl/octyl dodecyl)lauroyl glutamate (6) | Skin | Cosmetic milky lotion A | Before electrostatic spraying | 5 |
| | 6 | Ethanol (80) | Polyvinyl butyral (14) | Di(phytosteryl/octyl dodecyl)lauroyl glutamate (6) | Skin | Oil A | Before electrostatic spraying | 5 |
| | 7 | Ethanol (80) | Polyvinylacetal diethylamino acetate (14) | Di(phytosteryl/octyl dodecyl)lauroyl glutamate (6) | Skin | Lotion A | Before electrostatic spraying | 5 |
| | 8 | Ethanol (80) | Polyvinylacetal diethylamino acetate (14) | Di(phytosteryl/octyl dodecyl)lauroyl glutamate (6) | Skin | Cosmetic milky lotion A | Before electrostatic spraying | 5 |
| | 9 | Ethanol (80) | Polyvinylacetal diethylamino acetate (14) | Di(phytosteryl/octyl dodecyl)lauroyl glutamate (6) | Skin | Oil A | Before electrostatic spraying | 5 |

TABLE 3-continued

| | | Composition | | Portion subjected to electrostatic spraying | Liquid agent | | Adhesion evaluation |
|---|---|---|---|---|---|---|---|
| | Component (a) (%) | Component (b) (%) | Other component | | Type | Application time | |
| 10 | Ethanol (52) 1-Butanol (26) | Polyacrylic acid (22) | | Skin | Lotion A | After electrostatic spraying | 4 |
| 11 | Ethanol (52) 1-Butanol (26) | Polyacrylic acid (22) | | Skin | Cosmetic milky lotion A | After electrostatic spraying | 4 |
| 12 | Ethanol (52) 1-Butanol (26) | Polyacrylic acid (22) | | Skin | Oil A | After electrostatic spraying | 5 |
| 13 | Ethanol (80) | Polyvinyl butyral (14) | Di(phytosteryl/octyl dodecyl)lauroyl glutamate (6) | Skin | Lotion A | After electrostatic spraying | 5 |
| 14 | Ethanol (80) | Polyvinyl butyral (14) | Di(phytosteryl/octyl dodecyl)lauroyl glutamate (6) | Skin | Cosmetic milky lotion A | After electrostatic spraying | 5 |
| 15 | Ethanol (80) | Polyvinyl butyral (14) | Di(phytosteryl/octyl dodecyl)lauroyl glutamate (6) | Skin | Oil A | After electrostatic spraying | 5 |
| 16 | Ethanol (80) | Polyvinylacetal diethylamino acetate (14) | Di(phytosteryl/octyl dodecyl)lauroyl glutamate (6) | Skin | Lotion A | After electrostatic spraying | 5 |
| 17 | Ethanol (80) | Polyvinylacetal diethylamino acetate (14) | Di(phytosteryl/octyl dodecyl)lauroyl glutamate (6) | Skin | Cosmetic milky lotion A | After electrostatic spraying | 5 |
| 18 | Ethanol (80) | Polyvinylacetal diethylamino acetate (14) | Di(phytosteryl/octyl dodecyl)lauroyl glutamate (6) | Skin | Oil A | After electrostatic spraying | 5 |

Ethanol: Ethanol (99.5), special grade (Wako Pure Chemical Industries, Ltd.)
1-Butanol: 1-Butanol, special grade (Wako Pure Chemical Industries, Ltd.)
2-Propanol (Wako Pure Chemical Industries, Ltd.)
Di(phytosteryl/octyl dodecyl)lauroyl glutamate: Eldew PS-203 (Ajinomoto Co., Inc.)
Polyacrylic acid: Dermacryl 79 (Akzo Nobel)
Polyvinyl butyral: S-LEC B BM-1 (Sekisui Chemical Co., Ltd.)
Polyvinylacetal diethylamino acetate: AEA (Mitsubishi-Kagaku Foods Corporation)

TABLE 4

| | | | Composition | | Portion subjected to electrostatic spraying | Liquid agent | | Adhesion evaluation |
|---|---|---|---|---|---|---|---|---|
| | | Component (a) (%) | Component (b) (%) | Other component | | Type | Application time | |
| Ex. | 19 | 2-Propanol (79.7) | Polyvinyl butyral (14.5) | Di(phytosteryl/octyl dodecyl)lauroyl glutamate (5.8) | Skin | Lotion A | Before electrostatic spraying | 5 |
| | 20 | 2-Propanol (79.7) | Polyvinyl butyral (14.5) | Di(phytosteryl/octyl dodecyl)lauroyl glutamate (5.8) | Skin | Cosmetic milky lotion A | Before electrostatic spraying | 5 |
| | 21 | 2-Propanol (79.7) | Polyvinyl butyral (14.5) | Di(phytosteryl/octyl dodecyl)lauroyl glutamate (5.8) | Skin | Oil A | Before electrostatic spraying | 5 |
| | 22 | 2-propanol (79.7) | Polyvinyl butyral (14.5) | Di(phytosteryl/octyl dodecyl)lauroyl glutamate (5.8) | Skin | Lotion A | After electrostatic spraying | 5 |
| | 23 | 2-Propanol (79.7) | Polyvinyl butyral (14.5) | Di(phytosteryl/octyl dodecyl)lauroyl glutamate (5.8) | Skin | Cosmetic milky lotion A | After electrostatic spraying | 5 |
| | 24 | 2-propanol (79.7) | Polyvinyl butyral (14.5) | Di(phytosteryl/octyl dodecyl)lauroyl glutamate (5.8) | Skin | Oil A | After electrostatic spraying | 5 |
| | 25 | 100% Ethanol (79.6) water(0.4) | Polyvinyl butyral (14) | Di(phytosteryl/octyl dodecyl)lauroyl glutamate (6) | Skin | Lotion A | After electrostatic spraying | 5 |
| Com. Ex. | 1 | Ethanol (52) 1-Butanol (26) | Polyacrylic acid (22) | | Skin | | None | 1 |
| | 2 | Ethanol (80) | Polyvinyl butyral (14) | Di(phytosteryl/octyl dodecyl)lauroyl glutamate (6) | Skin | | None | 1 |

TABLE 4-continued

| | Composition | | | Portion subjected to electrostatic spraying | Liquid agent | | Adhesion evaluation |
|---|---|---|---|---|---|---|---|
| | Component (a) (%) | Component (b) (%) | Other component | | Type | Application time | |
| 3 | Ethanol(80) | Polyvinylacetal diethylamino acetate (14) | Di(phytosteryl/octyl dodecyl)lauroyl glutamate (6) | Skin | None | | 1 |
| 4 | Ethanol (80) | Polyvinyl butyral (14) | Di(phytosteryl/octyl dodecyl)lauroyl glutamate (6) | Plate | Lotion A | Before sheet is applied | 3 |
| 5 | Ethanol (80) | Polyvinyl butyral (14) | Di(phytosteryl/octyl dodecyl)lauroyl glutamate (6) | Plate | Cosmetic milky lotion A | Before sheet is applied | 3 |
| 6 | Ethanol (80) | Polyvinyl butyral (14) | Di(phytosteryl/octyl dodecyl)lauroyl glutamate (6) | Plate | Oil A | Before sheet is applied | 3 |
| 7 | Ethanol (80) | Polyvinyl butyral (14) | Di(phytosteryl/octyl dodecyl)lauroyl glutamate (6) | Plate | Lotion A | After sheet is applied | 3 |
| 8 | Ethanol (80) | Polyvinyl butyral (14) | Di(phytosteryl/octyl dodecyl)lauroyl glutamate (6) | Plate | Cosmetic milky lotion A | After sheet is applied | 3 |
| 9 | Ethanol (80) | Polyvinyl butyral (14) | Di(phytosteryl/octyl dodecyl)lauroyl glutamate (6) | Plate | Oil A | After sheet is applied | 3 |

Ethanol: Ethanol (99.5), special grade (Wako Pure Chemical Industries, Ltd.)
1-Butanol: 1-Butanol, special grade (Wako Pure Chemical Industries, Ltd.)
2-Propanol (Wako Pure Chemical Industries, Ltd.)
Di(phytosteryl/octyl dodecyl)lauroyl glutamate: Eldew PS-203 (Ajinomoto Co., Inc.)
Polyacrylic acid: Dermacryl 79 (Akzo Nobel)
Polyvinyl butyral: S-LEC B BM-1 (Sekisui Chemical Co., Ltd.)
Polyvinylacetal diethylamino acetate: AEA (Mitsubishi-Kagaku Foods Corporation)
*Comparative Examples are examples that the coating is formed on the place other than skin in advance by electrostatic spraying, and the coating is applied on skin.

As is clear from the results shown in Table 3 and Table 4, it is found that the coatings formed with the methods of the examples have a higher adhesion to the skin than those of the coatings formed with the methods of the comparative examples. Although not shown in the table, the color (white color) of the fibers was visually confirmed in the coatings formed with the methods of the comparative examples when the coatings were visually observed, whereas the transparency was confirmed in the coatings formed with the methods of the examples.

Test 2

The liquid agent used in the liquid agent applying step and the application amount thereof were changed as shown in Table 5, and the adhesion between the skin and the coating was evaluated as in the same manner as in Test 1. The spray composition used in this test was the same as the composition used in Example 4 in Test 1. In this test, the adhesion between the skin and the coating was evaluated in each liquid agent as following steps (1) or (2).

(1) the liquid agent applying step, and the electrostatic splaying step was performed in this order. ("Before splaying" shown in Table 5)

(2) the electrostatic splaying step, and the liquid agent applying step was performed in this order. ("After splaying" shown in Table 5)

Furthermore, in (1) of "Before splaying", adhesion was evaluated just after the liquid agent is applied (5 minutes after) and just after the liquid agent is applied (60 minutes after).

TABLE 5

| Liquid agent | 1 | 2 | 3 | 4 | 5 | 6 | 7 | 8 |
|---|---|---|---|---|---|---|---|---|
| Squalane | 10 | | | | | | | |
| Dimethyl silicone oil | 3 | 13 | 3 | 3 | 3 | | | |
| Light isoparaffin | | | 10 | | | | | |
| Neopentyl glycol dicaprate | | | | 10 | 30 | | | |
| Jojoba oil | | | | | | 100 | | |
| Polyethylene glycol | | | | | | | 10 | |
| 1,3-Butylene glycol | | | | | | | | 10 |
| Phenoxyethanol | 0.35 | 0.35 | 0.35 | 0.35 | 0.35 | | | |
| Acrylates/C10-30 alkyl acrylate crosspolymer | 0.3 | 0.3 | 0.3 | 0.3 | 0.3 | | | |
| 48% KOH aqueous solution | 0.07 | 0.07 | 0.07 | 0.07 | 0.07 | | | |
| EDTA•2Na | 0.01 | 0.01 | 0.01 | 0.01 | 0.01 | | | |
| Polyoxyethylene (20) 2-hexyldecyl ether | | | | | 0.4 | | | |
| Purified water | Remaining | Remaining | Remaining | Remaining | Remaining | | Remaining | Remaining |
| Total | 100 | 100 | 100 | 100 | 100 | 100 | 100 | 100 |
| Total amount of liquid agent applied (mg) | 85 | 73 | 96 | 90 | 98 | 30 | 160 | 148 |
| Basis weight of liquid agent (g/m$^2$) | 43.3 | 37.2 | 48.9 | 45.8 | 49.9 | 15.3 | 81.5 | 75.4 |

TABLE 5-continued

| Liquid agent | | 1 | 2 | 3 | 4 | 5 | 6 | 7 | 8 |
|---|---|---|---|---|---|---|---|---|---|
| Basis weight of liquid oil or polyol (g/m$^2$) | | 5.6 | 4.8 | 6.4 | 6 | 16.5 | 15.3 | 8.1 | 7.5 |
| Evaluation of adhesion | (1) Before splaying (5 min. after) | 5 | 5 | 5 | 5 | 5 | 5 | 5 | 5 |
| | (2) After splaying (5 min. after) | 5 | 5 | 5 | 5 | 5 | 5 | 5 | 5 |
| | (3) Before splaying (60 min. after) | 4 | 4 | 4 | 5 | 4 | 4 | 3 | 5 |

Dimethyl silicone oil: KF-96A-6cs (kinetic viscosity 10 mm$^2$/s Shin-Etsu Chemical Co. Ltd.)
Light isoparaffin: Parleam EX (NOF Corporation)
Neopentyl glycol dicaprate: Estemol N01 (The Nisshin OilliO Group, Ltd)
Phenoxyethanol: Hisolve EPH (Toho Chemical Industry Co., Ltd.)
Acrylates/C10-30 alkyl acrylate crosspolymer: Pemulen TR-2 (Lubrizol Advanced Materials)
EDTA•2Na: Clewat N (Nagase ChemteX Corporation)
Polyoxyethylene (20) 2-hexyldecyl ether: Emulgen 1620 (Kao Corporation)

As is clear from the results shown in Table 5, it is found that the strong adhesive coating to skin is formed in spite of changing polyol or oil types used for the liquid agent. It was found that the coating formed in Examples has transparency.

INDUSTRIAL APPLICABILITY

According to the present invention, the adhesion between the skin and the coating formed by electrostatic spraying is enhanced.

The invention claimed is:

1. A coating formation method for forming a coating on a surface of skin, comprising:
    applying, on skin, a liquid agent comprising at least one member selected from the group consisting of a polyol and an oil that is in a liquid form at 20° C., and mixtures thereof; and
    electrostatically spraying a composition directly on the skin to form a coating comprising a deposit of continuous fibers,
    wherein the applying and the electrostatic spraying are performed in this order or in a reversed order, and
    the composition consists of component (a), component (b), and optionally component (c):
    (a) 50 to 98 mass % of one or more volatile substances selected from the group consisting of ethanol, isopropyl alcohol, 1-butyl alcohol, and mixtures thereof;
    (b) 2 to 50 mass % of one or more water-insoluble polymers having a coating formation ability selected from the group consisting of polyvinylacetal diethylamino acetate, polyvinyl butyral, and polyacrylic acid; and
    (c) optionally one or more components selected from the group consisting of a plasticizer for the polymer having a coating formation ability to be used as the component (b), a coloring pigment, an extender pigment, a dye, a surfactant, a UV protection agent, a flavoring agent, a repellent, an antioxidant, a stabilizer, an antiseptic, and a vitamin,
    and
    wherein said continuous fibers have a length which is at least 100 times greater than their thickness, and
    wherein said continuous fibers have a thickness of 10 nm to 3,000 nm, and
    wherein said continuous fibers are formed from said water-insoluble polymer and accumulated on said skin during said electrostatic spraying.

2. The coating formation method according to claim 1, wherein in the electrostatic spraying, the composition is electrostatically sprayed on the skin to form a porous coating.

3. The coating formation method according to claim 1, wherein in the electrostatic spraying, a porous coating comprising the deposit of continuous fibers is formed, and then
    in the applying, the liquid agent is applied on the porous coating to form a liquid agent holding coating in which the liquid agent is present between the continuous fibers included in the porous coating and/or on the surfaces of the continuous fibers.

4. The coating formation method according to claim 1, wherein in the applying, the liquid agent is applied on the coating to maintain transparency of the coating.

5. The coating formation method according to claim 1, wherein in the electrostatic spraying, an electrostatic spraying apparatus is used to electrostatically spray the composition on the skin to form a porous coating comprising the deposit of fibers, and
    the electrostatic spraying apparatus comprises:
    a container in which the composition is accommodated;
    a nozzle from which the composition is discharged;
    a supply device that supplies the composition accommodated in the container to the nozzle; and
    a power source that applies a voltage to the nozzle.

6. The coating formation method according to claim 1, wherein said coating on a surface of skin has a structure in which said liquid agent is present between said continuous fibers in said coating comprising a deposit of continuous fibers and/or on surfaces of said continuous fibers in said coating comprising a deposit of continuous fibers.

7. The coating formation method according to claim 1, wherein said liquid agent further comprises water.

8. The coating formation method according to claim 1, wherein said liquid agent is selected from the group consisting of an O/W emulsion and a W/O emulsion.

9. The coating formation method according to claim 1, wherein said liquid agent is selected from the group consisting of a lotion and a cosmetic cream.

10. The coating formation method according to claim 1, wherein said liquid agent comprises an oil that is in a liquid form at 20° C.

11. The coating formation method according to claim 10, wherein said oil that is in a liquid form at 20° C. is selected from the group consisting of a hydrocarbon oil, an ester oil, a silicone oil, and mixtures thereof.

12. The coating formation method according to claim 10, wherein said oil that is in a liquid form at 20° C. is a silicone oil and is present in an amount of 10% mass or less.

13. The coating formation method according to claim 10, wherein said oil that is in a liquid form at 20° C. is selected from the group consisting of isododecane, isohexadecane, and hydrogenated polyisobutene, and mixtures thereof, which have a viscosity of less than 10 mPa·s at 30° C., and is present in an amount of 10 mass % or less.

14. The coating formation method according to claim 1, wherein said liquid agent comprises water and a polyol.

15. The coating formation method according to claim 1, wherein said liquid agent comprises an oil that is in a liquid form at 20° C. in an amount of 5 mass % or more.

16. The coating formation method according to claim 1, wherein said liquid agent comprises a polyol or an oil that is in liquid form at 20° C. in an amount of 5 mass % or more.

17. The coating formation method according to claim 1, wherein said liquid agent is applied to said skin in an amount of 5 g/m² to 50 g/m².

18. The coating formation method according to claim 1, wherein said composition comprises said component (b) in an amount of 6 mass % to 45 mass %, based on the mass of the composition.

19. The coating formation method according to claim 1, wherein said component (b) is polyvinyl butyral.

20. The coating formation method according to claim 1, wherein said continuous fibers in said coating comprising a deposit of continuous fibers are derived from said (b) water-insoluble polymer.

* * * * *